US00PP09271P

United States Patent [19]

Hoff

[11] Patent Number: Plant 9,271

[45] Date of Patent: Aug. 29, 1995

[54] VARIETY OF LILIUM NAMED 'HOLEBY'

[75] Inventor: Petrus M. M. Hoff, Steenbergen, Netherlands

[73] Assignee: Hoffgaarde B.V., Netherlands

[21] Appl. No.: 312,213

[22] Filed: Sep. 26, 1994

[51] Int. Cl.[6] ..... A01H 5/00
[52] U.S. Cl. ..... Plt./87.4
[58] Field of Search ..... Plt. 87.4

[56] References Cited

U.S. PATENT DOCUMENTS

P.P. 7,161 2/1990 Freeman-McRae ..... Plt./68

*Primary Examiner*—James R. Feyrer
*Attorney, Agent, or Firm*—Webb Ziesenheim Bruening Logsdon Orkin & Hanson

[57] ABSTRACT

A new and distinct cultivar of lily plant named Holeby, particularly characterized by ivory-blushed-with-pink upper surface and ivory lower surface of the flowers, height of about 30–40 cm, pedicel of 10–12 cm in length with 4–7 flowers, flowers often having more than 6 and up to 9–10 petals, filaments often changed to petals and capable of producing stems and flowers for cut-flower production.

1 Drawing Sheet

BACKGROUND OF THE INVENTION

The present inention comprises a new and distinct cultivar of lily, botanically known as *Lilium asiatic* and hereinafter referred to by the cultivar name Holeby.

The new cultivar is a product of a planned breeding program which had the objectives of creating new pot lily cultivars.

The new cultivar was originated from a hybridization made by the inventor Messr. Petrus Mattheus Maria Hoff in a controlled breeding program at Hoffgaarde B.V., Franseweg 9, 4651 PV Steenbergen, The Netherlands in 1989. The female and male parents were unnamed seedlings originated by applicant, which were proprietary and maintained by applicant for breeding purposes.

The new cultivar was discovered and selected as one flowering plant within the progeny of the stated cross by the inventor on May 15, 1991 in a controlled environment in Steenbergen.

The first act of asexual reproduction of the new cultivar was accomplished by the inventor when scales were taken from the initial selection on Nov. 11, 1991 in a controlled environment in Steenbergen.

Horticultural examination of clonal progeny initiated Mar. 30, 1992 has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light, intensity, and day length. The following observations, measurements, and comparisons describe plants grown in Steenbergen under greenhouse conditions which approximate those generally used in commercial practice.

The following traits have been repeatedly observed and are determined to be basic characteristics of the new cultivar which in combination distinguish this lily as a new and distinct cultivar.

(1) Flower color having an interesting ivory-blushed-with-pink character, with tepals having an essentially ivory ground color with numerous spots centrally with soft but progressively more intensive pink blush with progressive proximity to the apex of each tepal.

(2) Plant height of about 30–40 cm.

(3) Pedicel 10–12 cm in length with 4–7 flowers.

(4) Flowers often have more than 6 and up to 9–10 petals.

(5) Filaments are often transformed to petals.

(6) A pot lily.

DESCRIPTION OF THE DRAWING

The accompanying color photographic drawing shows typical flower characteristics of the new cultivar, with colors being as true as possible with illustrations of this type.

DESCRIPTION OF THE NEW PLANT

In the following description, color references are made to The Royal Horticultural Society Colour Chart. The color values were determined at Steenbergen on Mar. 20, 1992.

THE PLANT

Classification:
- *Botanic.*—*Lilium asiatic.*
- *Commercial.*—Hybrid *asiatic* lily for cut-flower production.

Form: Single upright stem from each bulb.
- *Height.*—30–40 cm.
- *Growth habit.*—Upright, erect, strong.

Stem:
- *Diameter.*—1 cm average.
- *Form.*—Rounded.
- *Color.*—Yellow-Green Group 148B.

Foliage:
- *Quantity.*—100–110 leaves.
- *Size of leaf.*—About 7 cm maximum length and 1.4 cm wide.
- *Shape of leaf.*—Narrow elliptic.
- *Texture of leaf.*—Smooth.
- *Color.*—Yellow-Green Group 147A.

Bulbs:
- *Size.*—Average 10–16 cm in circumference.
- *Stem bulblets.*—None.

THE BUD

Form: Broad oblong.
Size: 6 cm in length.
Number: 4–6 from bulb of 10–12 cm in circumference, 5–8 from bulb of 12–14 cm in circumference, 7–9 from bulb of 14–16 cm in circumference, 8–12 from bulb over 16 cm in circumference.
Color: Greyed-Purple Group 186B.

THE FLOWER

Blooming habit: 65 days after planting.
Size: 10 cm in diameter.
Borne: Umbellate.
Tepalage:
*Number of tepals.*—Six normal tepals, with none to four additional tepals, some of which frequently being the result of the incomplete transformation of one or more stamens. This wide variability of expression is characteristic of every specimen.
*Arrangement.*—True tepals occur in layers of threes, with the tepals of each layer in imbricated relation; additional complete or incomplete tepals generally follow the same arrangement and may form at least one additional complete tepal layer.
*Upper surface.*—Color: Throat area into heart area is White Group 155A; heart area blends into outer area of Red-Purple Group 65A.
*Spotting.*—Spots, Greyed-Orange Group 177A, are prolific occurring from throat area to about halfway; spots are about 0.9 mm in diameter.
*Surface.*—Smooth with a feeling of thickness.

*Texture.*—Smooth, no papillae.
Pedicel:
*Length.*—5 cm.
*Form.*—Upright.
Nectaries:
*Color.*—Greyed-Yellow Group 162C.
*Size.*—Very small, about 0.8 cm.
Form:
*Normal tepals.*—Normal.
*Additional tepals.*—Malformed, vestigial or absent.
Disease resistance: No unusual problems have been observed.
Fragrance: None.
Lasting quality: This is a pot lily — the flower duration depends on number of flowers; with 10 flowers, about three weeks.

REPRODUCTIVE ORGANS

Stamens:
*Number.*—6 with the number of stamens decreased by the number of tepals or petaloids beyond 6.
*Length.*—4 cm.
Pistils: 1.
Color: Greyed-Orange Group 166A.
Ovaries-color: Yellow-Green Group 143A.
Ploidy: Diploid.
Fertility: No viable seeds when self crossed. 100–200 viable seeds per flower when crossed with another variety.

I claim:

1. A new and distinct variety of lily plant substantially as shown and described.

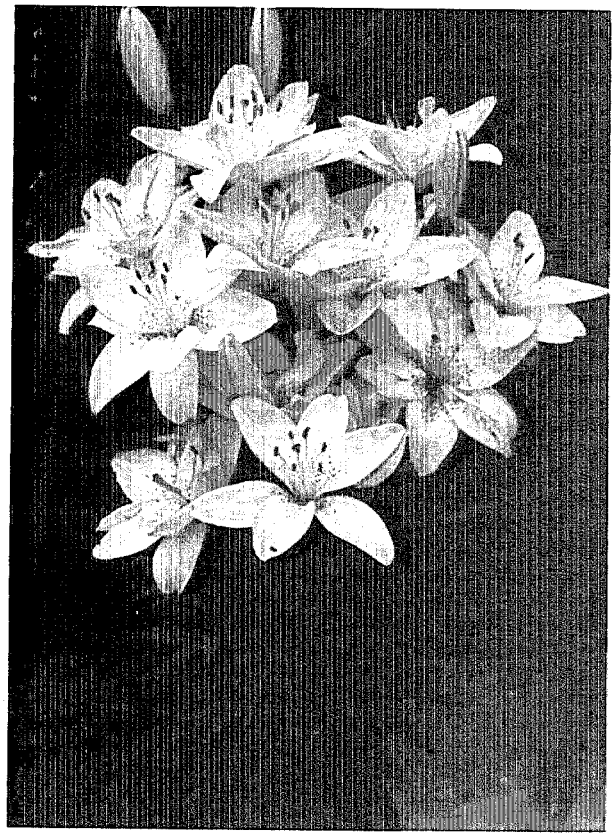

* * * * *